(12) United States Patent
Zierhofer

(10) Patent No.: US 8,798,758 B2
(45) Date of Patent: Aug. 5, 2014

(54) ELECTRICAL NERVE STIMULATION BASED ON CHANNEL SPECIFIC SAMPLING SEQUENCES

(75) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 354 days.

(21) Appl. No.: 13/070,880

(22) Filed: Mar. 24, 2011

(65) Prior Publication Data

US 2011/0230934 A1    Sep. 22, 2011

Related U.S. Application Data

(63) Continuation of application No. 11/685,887, filed on Mar. 14, 2007, now Pat. No. 7,937,157, which is a continuation of application No. 10/303,568, filed on Nov. 25, 2002, now Pat. No. 7,209,789, which is a continuation of application No. 09/648,687, filed on Aug. 25, 2000, now Pat. No. 6,594,525.

(60) Provisional application No. 60/150,773, filed on Aug. 26, 1999.

(51) Int. Cl.
*A61N 1/36* (2006.01)
*A61N 1/05* (2006.01)

(52) U.S. Cl.
CPC ........... *A61N 1/36032* (2013.01); *A61N 1/0541* (2013.01)
USPC .......................................................... 607/57

(58) Field of Classification Search
CPC .................... A61N 1/36032; A61N 1/0541
USPC ............................ 607/55, 56, 57, 137; 623/10
See application file for complete search history.

(56) References Cited

U.S. PATENT DOCUMENTS

| 4,284,856 A | 8/1981 | Hochmair et al. ......... 179/107 E |
| 4,428,377 A | 1/1984 | Zollner et al. ............. 128/419 R |
| 4,515,158 A | 5/1985 | Patrick et al. ............. 128/419 R |

(Continued)

FOREIGN PATENT DOCUMENTS

| EP | 1 854 504 A2 | 11/2007 | ............... A61N 1/36 |
| EP | 2208507 | 7/2010 | ............... A61N 1/36 |

(Continued)

OTHER PUBLICATIONS

Wilson, et al., "Better Speech Recognition With Cochlear Implants," *Nature*, 352, pp. 236-238, Jul. 1991.

(Continued)

*Primary Examiner* — Christopher D Koharski
*Assistant Examiner* — Frances Oropeza
(74) *Attorney, Agent, or Firm* — Sunstein Kann Murphy & Timbers LLP

(57) ABSTRACT

A method of activating at least two electrodes in a multichannel electrode array using channel specific sampling sequences is presented. A channel specific sampling sequence is defined for each electrode, the sequence having a particular duration, pulse amplitude distribution, and number of pulses. A weighting factor is applied to the channel specific sampling sequence. Each electrode in the multichannel electrode array is then simultaneously activated using sign-correlated pulses, the sign-correlated pulses based on parameters of spatial channel interaction reflecting geometric overlapping of electrical fields from each electrode, non-linear compression, and each electrode's weighted channel specific sampling sequence.

20 Claims, 7 Drawing Sheets

(56) References Cited

U.S. PATENT DOCUMENTS

| | | | | |
|---|---|---|---|---|
| 4,823,795 A | * | 4/1989 | van den Honert | 607/56 |
| 5,215,085 A | * | 6/1993 | von Wallenberg-Pachaly | 607/56 |
| 5,549,658 A | | 8/1996 | Shannon et al. | 607/57 |
| 5,597,380 A | | 1/1997 | McDermott et al. | 607/57 |
| 5,601,617 A | | 2/1997 | Loeb et al. | 607/56 |
| 5,603,726 A | | 2/1997 | Schulman et al. | 607/57 |
| 5,609,616 A | | 3/1997 | Schulman et al. | 607/56 |
| 5,626,629 A | | 5/1997 | Faltys et al. | 607/57 |
| 5,749,912 A | | 5/1998 | Zhang et al. | 607/57 |
| 5,824,022 A | | 10/1998 | Zilberman et al. | 607/57 |
| 5,938,691 A | | 8/1999 | Schulman et al. | 607/57 |
| 6,002,966 A | | 12/1999 | Loeb et al. | 607/57 |
| 6,175,767 B1 | | 1/2001 | Doyle, Sr. | 607/57 |
| 6,219,580 B1 | | 4/2001 | Faltys et al. | 607/57 |
| 6,289,247 B1 | | 9/2001 | Faltys et al. | 607/57 |
| 6,295,472 B1 | * | 9/2001 | Rubinstein et al. | 607/55 |
| 6,381,336 B1 | | 4/2002 | Lesinski et al. | 381/326 |
| 6,594,525 B1 | | 7/2003 | Zierhofer | 607/67 |
| 6,600,955 B1 | | 7/2003 | Zierhofer | 607/57 |
| 7,937,157 B2 | | 5/2011 | Zierhofer | 607/57 |
| 2001/0031909 A1 | | 10/2001 | Faltys et al. | 600/25 |
| 2004/0082985 A1 | | 4/2004 | Faltys et al. | 607/116 |

FOREIGN PATENT DOCUMENTS

| | | | | |
|---|---|---|---|---|
| WO | WO 98/49775 | 11/1998 | | H03H 17/06 |
| WO | WO 99/35882 | 7/1999 | | H04R 25/00 |
| WO | WO 99/49815 | 10/1999 | | A61F 2/18 |
| WO | WO 01/19304 | 3/2001 | | A61F 11/04 |
| WO | WO 2006/136961 | 12/2006 | | A61N 1/36 |

OTHER PUBLICATIONS

Wilson, et al., "Speech Processors for Auditory Prostheses," 7th Quarterly Progress Report, NIH Contract N01-DC-2-24-1 (Feb. 1, 1994-Apr. 30, 1994).

Kral, et al., "Spacial Resolution of Cochlear Implants: the Electrical Field and Excitation of Auditory Afferents," Hearing Research, 121, pp. 11-28 (1998).

Matsuoka, A.J., "Compound Action Potentials Evoked by Electrical Pulse Trains: Effects of Stimulus Parameters on Response Patterns," The Thesis at University of Iowa, Jul. 1998.

International Searching Authority, International Searching Authority, International Search Report, dated Nov. 16, 2005.

Loizou, "Signal Processing for Cochlear Prosthesis: A Tutorial Review," IEEE, vol. 2, pp. 881-885, 1997.

European Patent Office, Partial European Report—Application No. 07075655.6-2305, 7 pages, Nov. 5, 2008.

International Searching Authority, International Search Report, International Application No. PCT/IB2006/002510, dated Jan. 23, 2007, together with the Written Opinion of the International Searching Authority, 14 pages.

European Patent Office, European Application No. EP 10003323.2-2305, 6 pages, Jun. 22, 2010.

United States Patent and Trademark Office, Office Action dated Jan. 3, 2002, pertaining to U.S. Appl. No. 09/648,687, 13 pages.

Bromberg & Sunstein LLP, Response dated Apr. 2, 2002, pertaining to U.S. Appl. No. 09/648,687, 14 pages.

United States Patent and Trademark Office, Office Action dated Jun. 26, 2002, pertaining to U.S. Appl. No. 09/648,687, 7 pages.

Bromberg & Sunstein LLP, Response dated Sep. 11, 2002, pertaining to U.S. Appl. No. 09/648,687, 5 pages.

United States Patent and Trademark Office, Interview Summary dated Sep. 16, 2002, pertaining to U.S. Appl. No. 09/648,687, 10 pages.

United States Patent and Trademark Office, Advisory Action and Interview Summary dated Oct. 1, 2002, pertaining to U.S. Appl. No. 09/648,687, 6 pages.

Bromberg & Sunstein LLP, Amendment dated Nov. 25, 2002, pertaining to U.S. Appl. No. 09/648,687, 12 pages.

United States Patent and Trademark Office, Interview Summary dated Dec. 9, 2002, pertaining to U.S. Appl. No. 09/648,687, 2 pages.

United States Patent and Trademark Office, Notice of Allowance and Fee(s) Due dated Dec. 16, 2002, pertaining to U.S. Appl. No. 09/648,687, 9 pages.

Bromberg & Sunstein LLP, Election and Preliminary Amendment dated Mar. 3, 2006, pertaining to U.S. Appl. No. 10/303,568, 6 pages.

United States Patent and Trademark Office, Office Action dated Mar. 31, 2006, pertaining to U.S. Appl. No. 10/303,568, 8 pages.

Bromberg & Sunstein LLP, Response dated Sep. 28, 2006, pertaining to U.S. Appl. No. 10/303,568, 8 pages.

United States Patent and Trademark Office, Interview Summary dated Oct. 6, 2006, pertaining to U.S. Appl. No. 10/303,568, 4 pages.

United States Patent and Trademark Office, Notice of Allowance and Fee(s) Due dated Dec. 19, 2006, pertaining to U.S. Appl. No. 10/303,568, 5 pages.

United States Patent and Trademark Office, Office Action dated Jan. 31, 2008, pertaining to U.S. Appl. No. 11/101,149, 5 pages.

Bromberg & Sunstein LLP, Response dated Feb. 29, 2008, pertaining to U.S. Appl. No. 11/101,149, 7 pages.

United States Patent and Trademark Office, Office Action dated May 16, 2008, pertaining to U.S. Appl. No. 11/101,149, 10 pages.

Bromberg & Sunstein LLP, Response dated Aug. 15, 2008, pertaining to U.S. Appl. No. 11/101,149, 7 pages.

United States Patent and Trademark Office, Office Action dated Dec. 16, 2008, pertaining to U.S. Appl. No. 11/101,149, 12 pages.

Bromberg & Sunstein LLP, Response After Final Rejection dated Mar. 16, 2009, pertaining to U.S. Appl. No. 11/101,149, 8 pages.

United States Patent and Trademark Office, Advisory Action dated Apr. 1, 2009, pertaining to U.S. Appl. No. 11/101,149, 3 pages.

Bromberg & Sunstein LLP, Request for Continued Examination dated May 15, 2009, pertaining to U.S. Appl. No. 11/101,149, 12 pages.

United States Patent and Trademark Office, Office Action dated Jul. 30, 2009, pertaining to U.S. Appl. No. 11/101,149, 9 pages.

Sunstein Kann Murphy & Timbers LLP, Response dated Oct. 29, 2009, pertaining to U.S. Appl. No. 11/101,149, 13 pages.

United States Patent and Trademark Office, Office Action dated Mar. 4, 2010, pertaining to U.S. Appl. No. 11/101,149, 8 pages.

United States Patent and Trademark Office, Interview Summary dated Jul. 30, 2010, pertaining to U.S. Appl. No. 11/101,149, 4 pages.

Liang, et al., "A Method for Evaluating the Selectivity of Electrodes Implanted for Nerve Stimulation," IEEE Transactions on Biomedical Engineering, vol. 38, No. 5, pp. 443-449, May 1991.

European Patent Office, Examination Report—European Application No. 07075655/6-2305, dated Aug. 26, 2010, 4 pages.

European Patent Office, Communication Pursuant to Article 93(3) EPC—European Application No. 07075655.6-2305, dated Jun. 8, 2009, 1 page.

Clive Froud & Co. Limited, Response dated Oct. 12, 2009, pertaining to European Application No. 07075655.6-2305, 6 pages.

Sunstein Kann Murphy & Timbers LLP, Response to Restriction Requirement dated Apr. 30, 2010, pertaining to U.S. Appl. No. 11/685,887, 7 pages.

United States Patent and Trademark Office, Office Action dated Aug. 2, 2010, pertaining to U.S. Appl. No. 11/685,887, 6 pages.

United States Patent and Trademark Office, Interview Summary dated Sep. 29, 2010, pertaining to U.S. Appl. No. 11/685,887, 3 pages.

United States Patent and Trademark Office, Notice of Allowance dated Dec. 28, 2010, pertaining to U.S. Appl. No. 11/685,887, 15 pages.

* cited by examiner

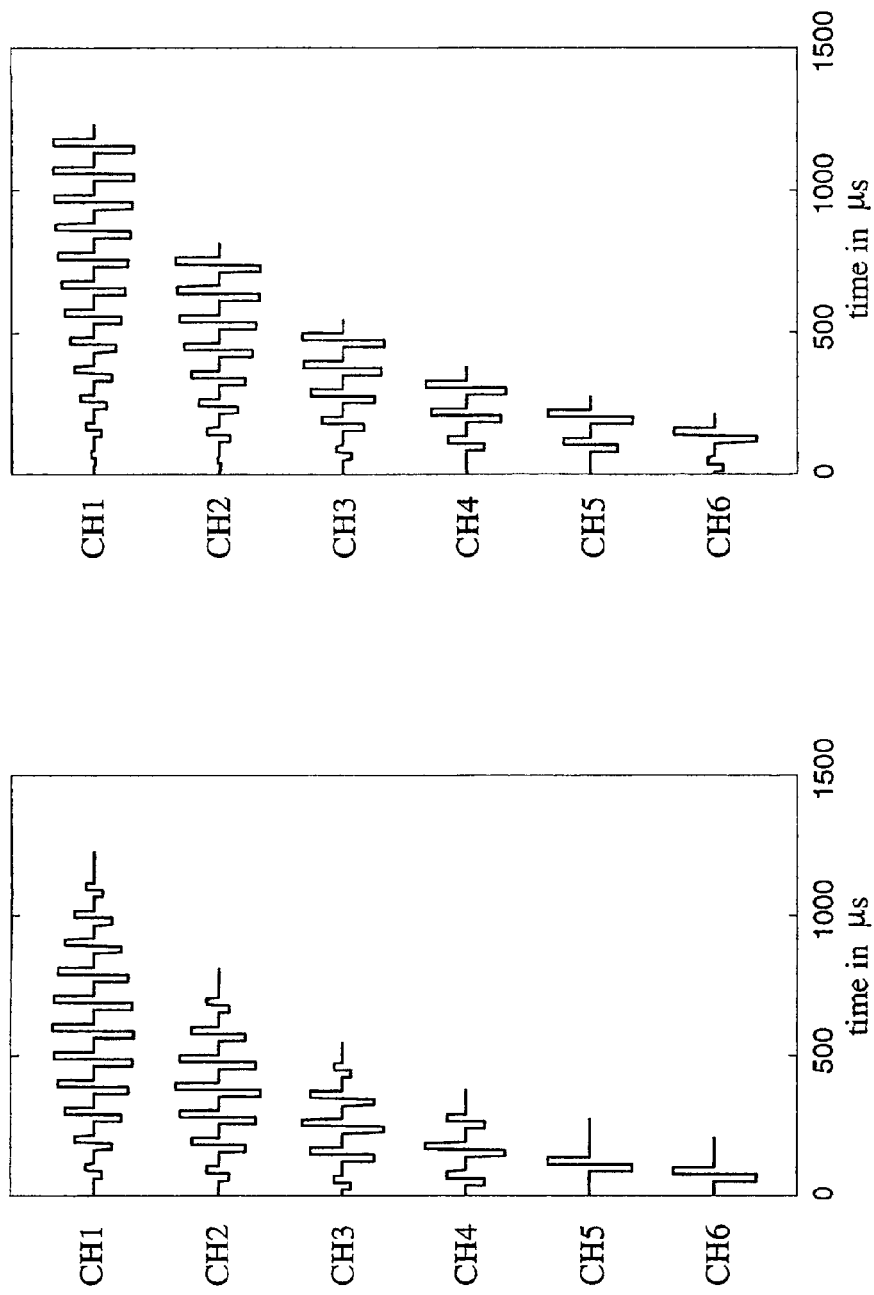

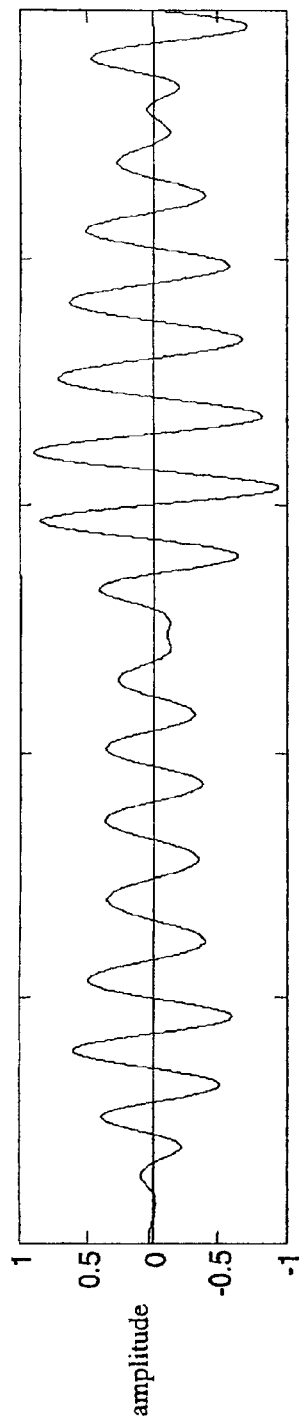
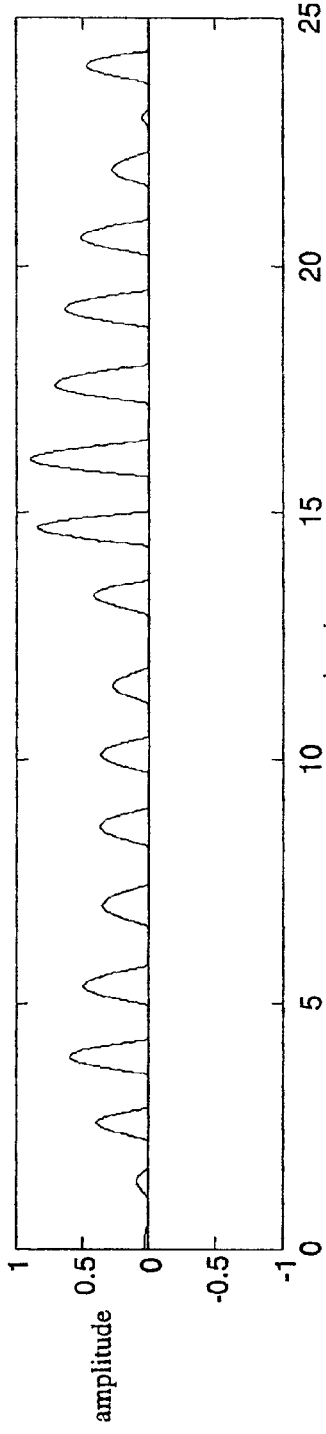
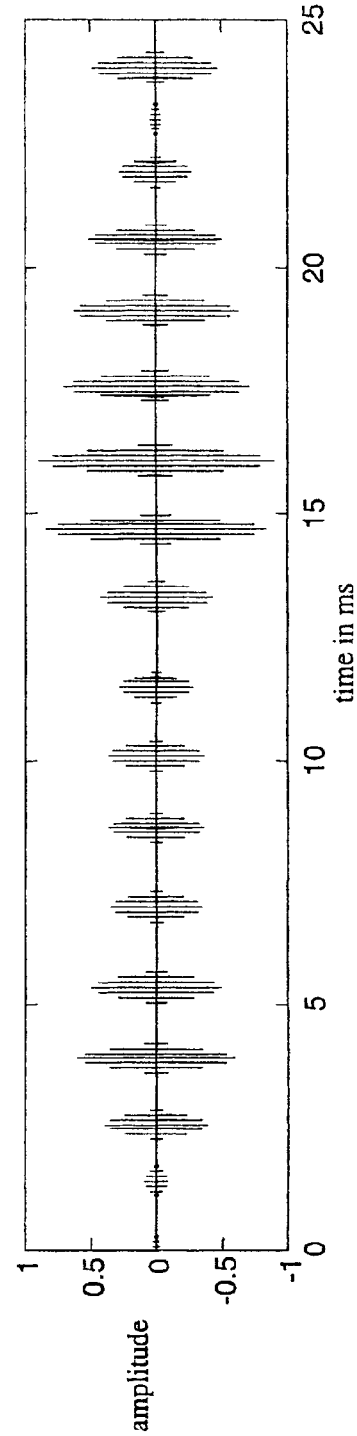
FIG. 2A
FIG. 2B
FIG. 2C

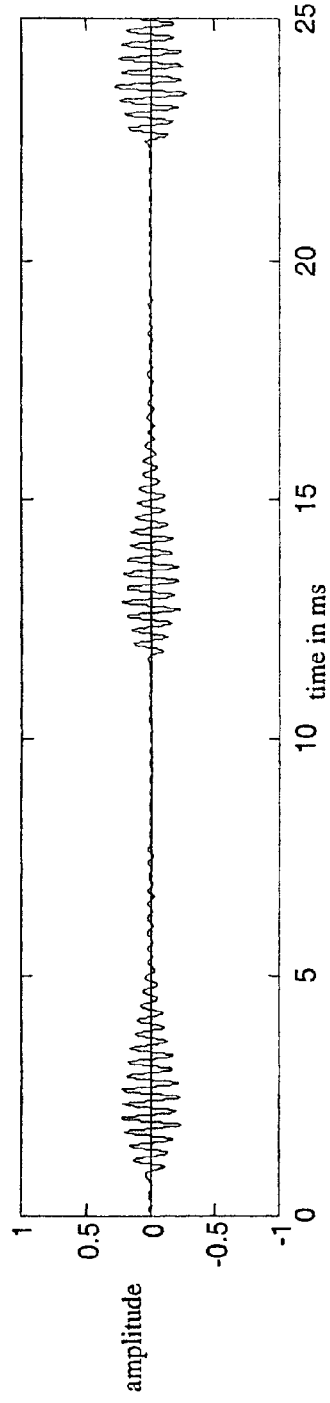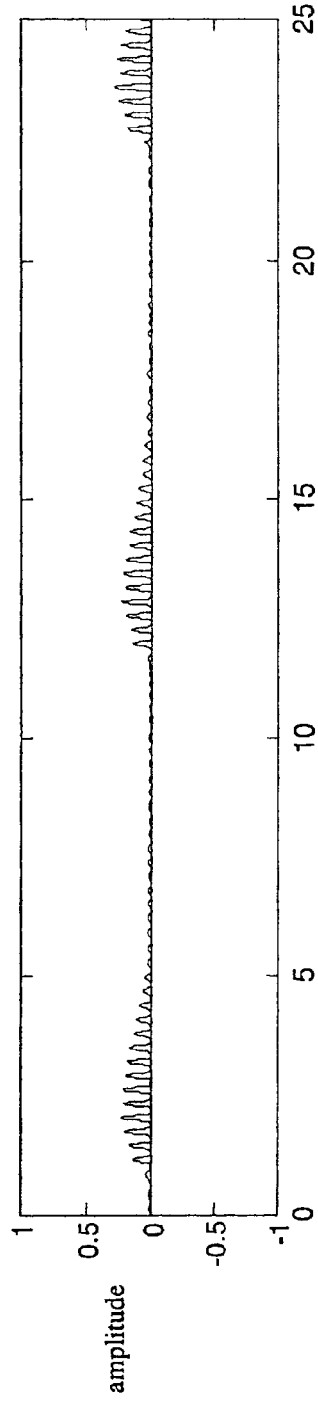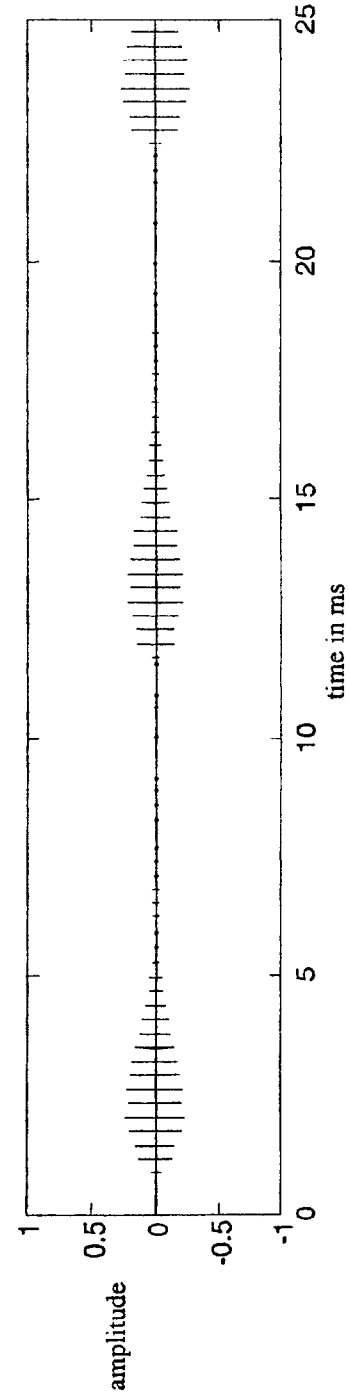
FIG. 3A
FIG. 3B
FIG. 3C

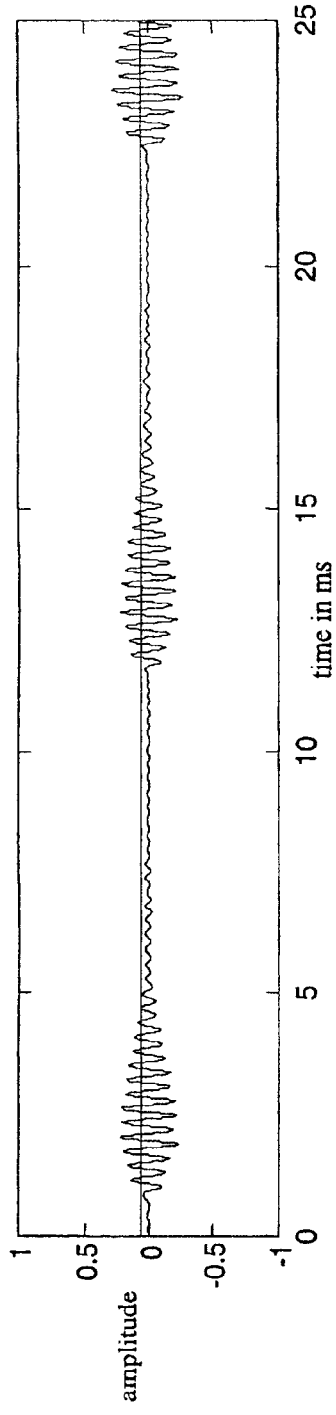
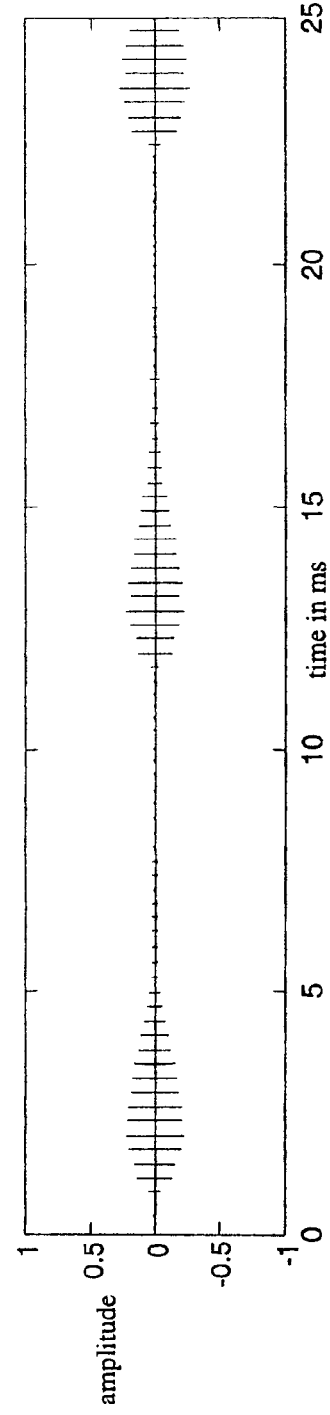
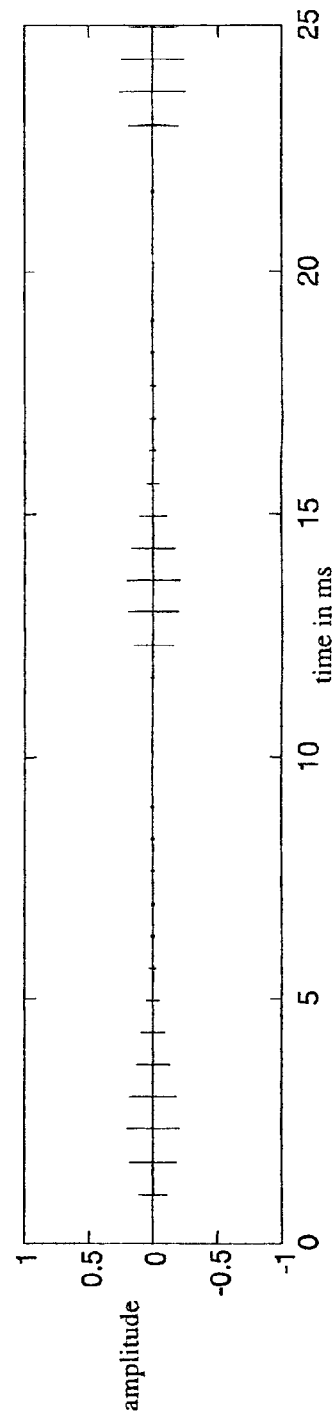

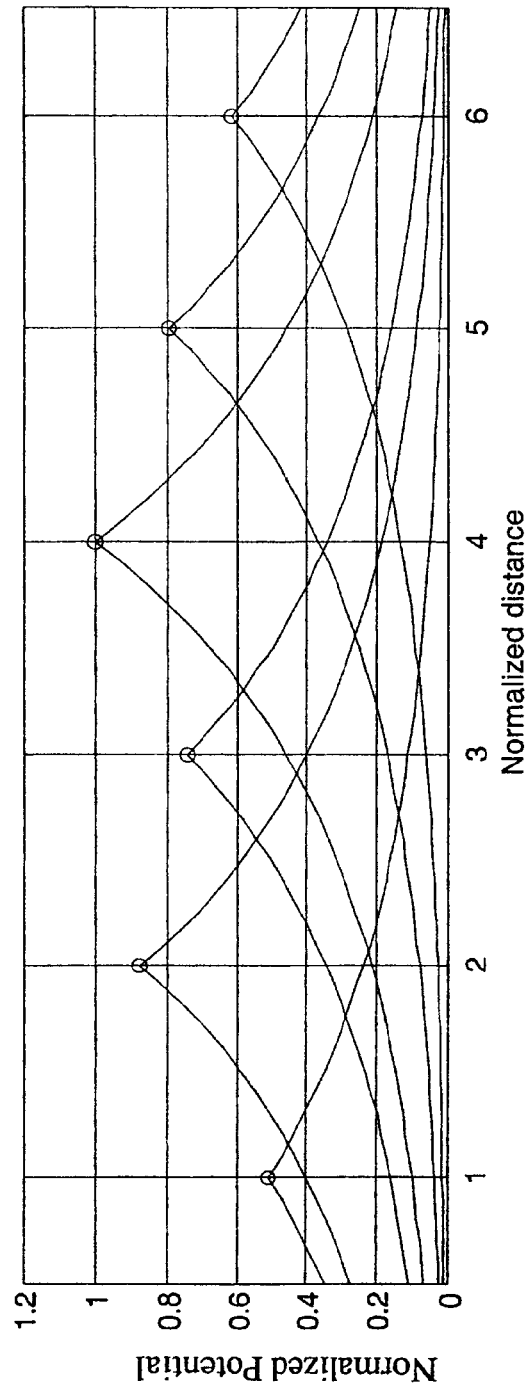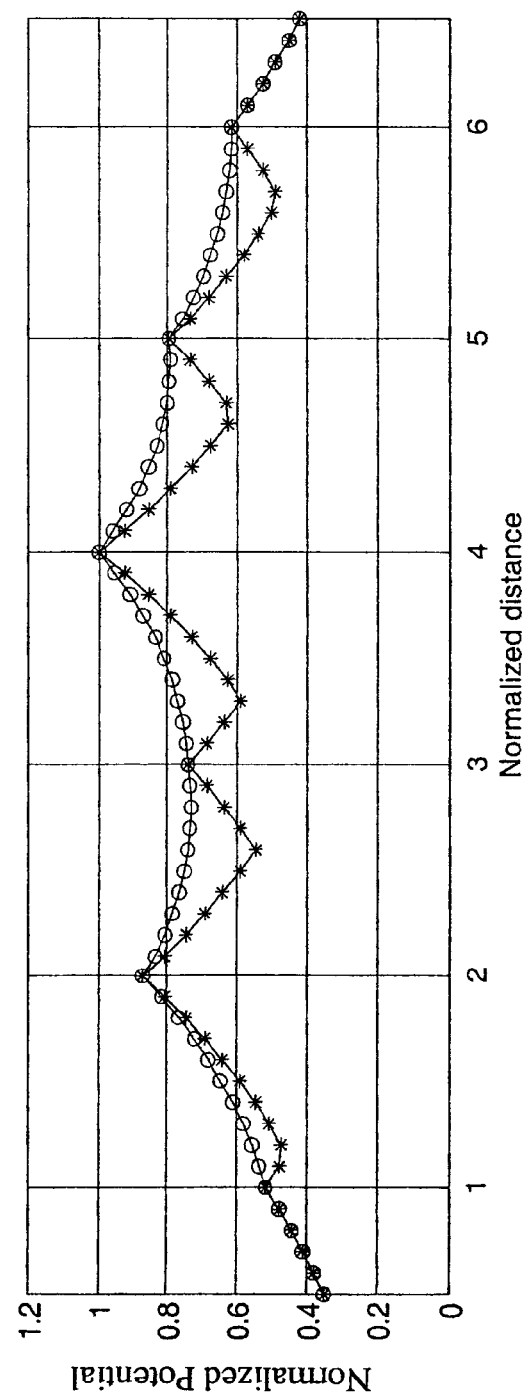

ELECTRICAL NERVE STIMULATION BASED ON CHANNEL SPECIFIC SAMPLING SEQUENCES

PRIORITY

This application is a continuation of U.S. application Ser. No. 11/685,887 filed Mar. 14, 2007, entitled Electrical Nerve Stimulation Based on Channel Specific Sampling Sequences, which in turn is a continuation of U.S. application Ser. No. 10/303,568 filed Nov. 25, 2002, entitled Electrical Nerve Stimulation Based on Channel Specific Sampling Sequences, which issued as U.S. Pat. No. 7,209,789, which in turn is a continuation of U.S. application Ser. No. 09/648,687 filed Aug. 25, 2000, entitled Electrical Nerve Stimulation Based on Channel Specific Sampling Sequences, which issued as U.S. Pat. No. 6,594,525, and which claims priority from U.S. provisional patent application Ser. No. 60/150,773 filed Aug. 26, 1999, entitled Concept for Electrical Stimulation of the Acoustic Nerve Based on Channel Specific Sampling Sequences (CSSS). Each of the above described applications are hereby incorporated herein by reference.

FIELD OF THE INVENTION

The present invention relates to electrical nerve stimulation, and more particularly, electrostimulation of the nerve based on channel specific sampling sequences.

BACKGROUND

Cochlear implants (inner ear prostheses) are a possibility to help profoundly deaf or severely hearing impaired persons. Unlike conventional hearing aids, which just apply an amplified and modified sound signal, a cochlear implant is based on direct electrical stimulation of the acoustic nerve. The intention of a cochlear implant is to stimulate nervous structures in the inner ear electrically in such a way that hearing impressions most similar to normal hearing are obtained.

A cochlear prosthesis essentially consists of two parts, the speech processor and the implanted stimulator. The speech processor contains the power supply (batteries) of the overall system and is used to perform signal processing of the acoustic signal to extract the stimulation parameters. The stimulator generates the stimulation patterns and conducts them to the nervous tissue by means of an electrode array which usually is positioned in the scala tympani in the inner ear. The connection between speech processor and stimulator is established either by means of a radio frequency link (transcutaneous) or by means of a plug in the skin (percutaneous).

At present, the most successful stimulation strategy is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991) [hereinafter Wilson et al., 1991], which is incorporated herein by reference. Signal processing for CIS in the speech processor involves the following steps:

(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals (step (3) of above). These signals are sampled sequentially, and the stimulation pulses are applied in a strictly non-overlapping sequence. Thus, as a typical CIS-feature, only one stimulation channel is active at one time. The overall stimulation rate is comparatively high. For example, assuming an overall stimulation rate of 18 kpps, and using an 12 channel filter bank, the stimulation rate per channel is 1.5 kpps. Such a stimulation rate per channel usually is sufficient for adequate temporal representation of the envelope signal.

The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is at the lower limit.

Each output of the CIS band pass filters can roughly be regarded as a sinusoid at the center frequency of the band pass filter, which is modulated by the envelope signal. This is due to the quality factor $Q \approx 3$ of the filters. In case of a voiced speech segment, this envelope is approximately periodic, and the repetition rate is equal to the pitch frequency.

In the current CIS-strategy, the envelope signals only are used for further processing, i.e., they contain the entire stimulation information. For each channel, the envelope is represented as a sequence of biphasic pulses at constant repetition rate. As a characteristic feature of CIS, this repetition rate (typically 1.5 kpps) is equal for all channels, and there is no relation to the center frequencies of the individual channels. It is intended that the repetition rate is not a temporal cue for the patient, i.e., it should be sufficiently high, so that the patient does not percept tones with a frequency equal to the repetition rate. The repetition rate is usually chosen greater than at twice the bandwidth of the envelope signals (Nyquist theorem).

SUMMARY OF THE INVENTION

In accordance with one aspect of the invention, electrodes in a multichannel electrode array are activated using channel specific sampling sequences. A channel specific sampling sequence for each electrode is defined, having a particular duration, amplitude, and number of pulses. A weighting factor is applied to the channel specific sampling sequence, creating a weighted channel specific sampling sequence. Each electrode in the multichannel electrode array is then simultaneously activated using sign-correlated pulses, the sign-correlated pulses based on parameters of spatial channel interaction, non-linear compression, and each electrode's weighted channel specific sampling sequence.

In accordance with other related embodiments, the electrodes stimulate the acoustic nerve. The multichannel electrode array can be used in a monopolar electrode configuration having a remote ground. The pulse amplitudes can be derived by sampling a signal waveform, for example, one half the period of a sinusoid between 0 and $\pi$, or one quarter of a sinusoid between 0 and $\pi/2$ so that the amplitude distribution is monotonically increasing. Symmetrical biphasic current pulses can be used to sample the signal waveform. The channel specific sampling sequence pulse rate may be between 5-10 kpps. The parameters of spatial channel interaction can be based on a single electrode model having exponential decays of the potentials at both sides of the electrode, the sign-correlated pulses having amplitudes which are calculated using properties of a tri-diagonal matrix. The multichannel electrode array can be in a cochlear implant, whereby the weighting factor is transmitted to the cochlear implant. Start and stop bits, and addresses associated with an electrode can also be transmitted to the cochlear implant.

In accordance with another embodiment of the invention, electrodes in a multichannel electrode array are activated using channel specific sampling sequences by applying an acoustic signal to a bank of filters, each filter in the bank of filters associated with a channel having an electrode. A weighting factor is derived for each channel based on the output of each channel's filter. The weighting factor is then applied to a channel specific sampling sequence having a particular duration, amplitude and number of pulses, creating a weighted channel specific sampling sequence. Each channel's electrode is simultaneously activated using sign-correlated pulses, the sign-correlated pulses based on the weighted channel specific sampling sequence, non-linear compression, and parameters of spatial channel interaction.

In accordance with other related embodiments, the electrodes can stimulate the acoustic nerve. The weighting factor can be derived by rectifying the output of each filter, and then determining the maximum amplitude of each half-wave in the rectified signal. The multichannel electrode array can used a monopolar electrode configuration having a remote ground. The pulse amplitudes of the channel specific sampling sequence can be derived by sampling a signal waveform, such as one half the period of a sinusoid between 0 and π, or one quarter of a sinusoid so that the amplitude distribution is monotonically increasing. Symmetrical biphasic current pulses can be used to sample the waveform. Each channel filter can be a bandpass filter. The duration and number of pulses in the channel specific sampling sequence can then be derived from the center frequency of the channel's bandpass filter. For example, the duration of the channel specific sampling sequence can be one half of the period of the bandpass filter's center frequency. The parameters of spatial channel interaction can be based on a single electrode model having exponential decays of the potentials at both sides of the electrode, the sign-correlated pulses having amplitudes determined by using properties of a tri-diagonal matrix. The multichannel electrode array can be in a cochlear implant, whereby the weighting factor is transmitted to the cochlear implant. Start and stop bits, and addresses associated with an electrode can also be transmitted to the cochlear implant.

In accordance with another embodiment of the invention, electrodes are simultaneously activated in a multichannel electrode array using channel specific sampling sequences. Sign-correlated pulses are used. The amplitudes of the sign-correlated pulses are calculated by taking into account parameters of spatial channel interaction. In calculating the amplitudes of the sign-correlated pulses a single electrode model having exponential decays of the potentials at both sides of the electrode can be used. The amplitudes of the sign-correlated pulses can be calculated using properties of a tri-diagonal matrix.

In accordance with another embodiment of the invention, channel specific sampling sequence having a pulse descriptive characterization are defined. The channel specific sampling sequence is used to activate electrodes in a multichannel electrode array, each filter in a bank of filters associated with a channel having an electrode. Pulse amplitudes of the channel sampling sequence are derived by sampling a signal waveform. The duration and number of pulses of the channel specific sampling sequence are derived from a frequency associated with the channel's filter.

In accordance with other related embodiments, the sampling is of a half period of a sinusoid between 0 and π. The sampling can also be of a quarter period of a sinusoid between 0 and π/2, so that pulse amplitude distribution monotonically increases. The sampling can use biphasic current pulses. Each filter can be a bandpass filter. The duration and number of pulses in the channel specific sampling sequence can be derived from the center frequency of the channel's bandpass filter. The duration of the channel specific sampling sequence can be one half of the period of the bandpass filter's center frequency.

In another embodiment of the invention, a weighting factor for a channel specific sampling sequence is derived, the channel specific sampling sequence being used to activate electrodes in a multichannel electrode array, each filter in a bank of filters associated with a channel having an electrode. The output of each filter is rectified, creating a half-wave rectified signal. The maximum amplitude of each half-wave in the half-wave rectified signal is then determined.

BRIEF DESCRIPTION OF THE DRAWINGS

The foregoing features of the invention will be more readily understood by reference to the following detailed description, taken with reference to the accompanying drawings, in which:

FIG. 1 shows channel specific sampling sequences (CSSS) for two 6-channel systems utilizing biphasic pulses at 10 kpp/s and phase duration of 25 μs
   a. derived from a sinusoid within [0 π]
   b. derived from a sinusoid within [0 π/2], amplitudes monotonically increasing
FIG. 2 shows stimulation with channel specific sampling sequences (CSSS)
   a. Band pass filter output signal (653 Hz-876 Hz)
   b. Half wave rectified band pass filter output
   c. Associated CSSS stimulation sequence
FIG. 3 shows stimulation with channel specific sampling sequences (CSSS)
   a. Bandpass filter output signal (3457 Hz-5500 Hz)
   b. Half wave rectified band pass filter output
   c. Associated CSSS stimulation sequence

FIG. 5 shows a comparison of stimulation patterns between CSSS and CIS
   a. Band pass filter output signal (3457 Hz-5500 Hz)
   b. CSSS stimulation sequence
   c. CIS stimulation sequence (envelope sampling with single pulses at 1.5 kpps)

FIG. 6 shows estimated potential distributions in the scala tympani ($\lambda$=3.6 mm, d=2.8 mm)
   a. Responses to single channel activation
   b. Effective Potential Distributions (asterisks for CIS, circles for CSSS)

DETAILED DESCRIPTION OF THE INVENTION

Figure 4A:
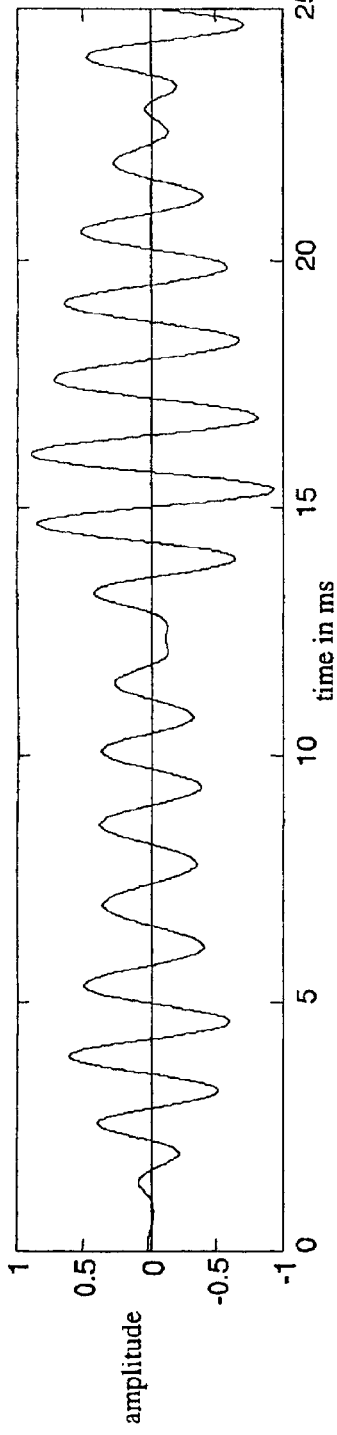
FIG. 4 shows a comparison of stimulation patterns between CSSS and CIS
   a. Band pass filter output signal (653 Hz-876 Hz)
   b. CSSS stimulation sequence
   c. CIS stimulation sequence (envelope sampling with single pulses at 1.5 kpps)

A cochlear implant with stimulation patterns containing enhanced temporal information, especially in the low frequency range up to 1 kHz, is described. It is known from literature that the neurons are able to track analogue electrical sinusoidals up to about 1 kHz. This ability is not exploited in the present CIS strategy, since the sampling rate is too low to represent high frequency envelope waveforms.

The stimulation strategy utilized is based on channel specific sampling sequences (CSSS). The basic idea is to a apply a stimulation pattern, where a particular relationship to the center frequencies of the filter channels is preserved, i.e., the center frequencies are represented in the temporal waveforms of the stimulation patterns, and are not fully removed, as in CIS.

Each stimulation channel is associated with a particular CSSS, which is a sequence of ultra-high-rate biphasic pulses (typically 5-10 kpps). Each CSSS has a distinct length (number of pulses) and distinct amplitude distribution. The length of a CSSS is derived from the center frequency of the associated band pass filter. A CSSS associated with a lower filter channel is longer than a CSSS associated with a higher filter channel. Typically, it is one half of the period of the center frequency. The amplitude distribution can be adjusted to patient specific requirements. For convenience, the amplitude of the maximum biphasic pulse within a CSSS is normalized to one. For illustration, two examples for a 6-channel system are shown. In FIG. 1(a), the CSSS's are derived by sampling one half of a period of a sinusoid, whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 µs. For channels #5 and #6, one half of a period of the center frequencies is too short to give space for more than one stimulation pulse, i.e., the "sequences" consist of only one pulse, respectively. In FIG. 1(b), the sequences are derived by sampling one quarter of a sinusoid with a frequency, which is half the center frequency of the band pass filters. These CSSS's have about the same durations as the CSSS's in FIG. 1(a), respectively, but the amplitude distribution is monotonically increasing. Such monotonic distributions might be advantageous, because each pulse of the sequence can theoretically stimulate neurons at sites which cannot be reached by its predecessors. This is a pure "geometric" effect, and could possibly result in a broader temporal distribution of the firing pattern of the neurons.

An example of a stimulation pattern based on CSSS is depicted in FIG. 2 for a voiced speech segment. For reasons of clarity, the influence of spatial channel interaction is neglected here. In addition, and in the following text, the instantaneous non-linear compression is omitted for convenience, however it is realized that such conversion is required for actual stimulation patterns. FIG. 2(a) shows the output of a band pass filter (cut off frequencies at 553 Hz and 876 Hz). FIG. 2(b) illustrates the half-wave rectified version of the signal. In FIG. 2(c), each half-wave-pulse is replaced by a CSSS, where the amplitude of the maximum pulse within each CSSS is equal to the maximum of the associated half-wave-pulse. Thus, FIG. 3 represents a sequence of weighted and time-shifted CSSS's. The CSSS used for this example is equal to the CSSS in FIG. 1(a) for channel CH2, and for convenience, each biphasic pulse is represented as a single vertical line.

An example of a stimulation pattern based on CSSS for a higher frequency channel is shown in FIG. 3 (the input speech segment is the same as for FIG. 2, spatial channel interaction is neglected again). The band pass filter here selects a range between 3475 Hz and 5500 Hz. With a center frequency of 4273 Hz, the period is 229 µs, and sampling one half of this period gives space for only one pulse (cf. CSSS as shown in FIG. 1 for channel CH5). Here, the envelope sampling is reduced to a sampling with single pulses at a rate equal to about the center frequency of 4273 Hz.

Figure 4B:
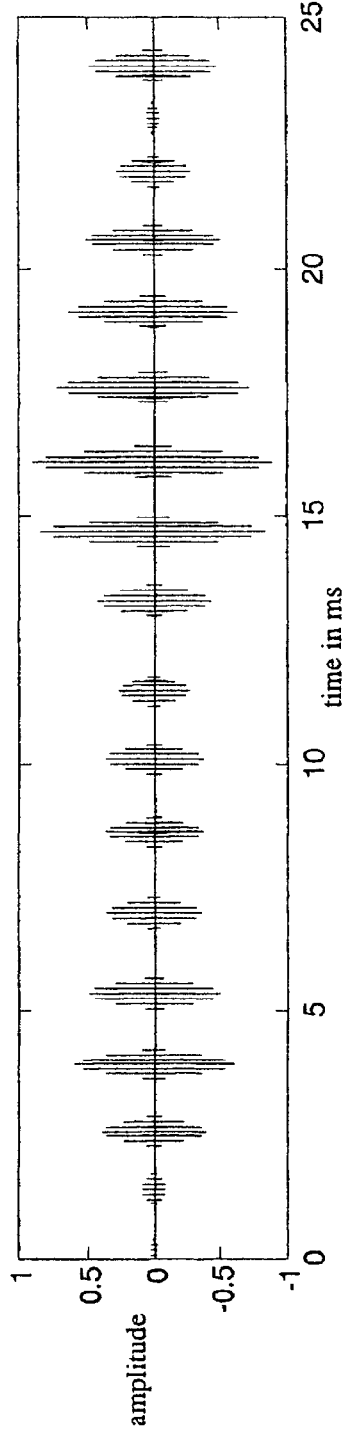
Figure 4C:
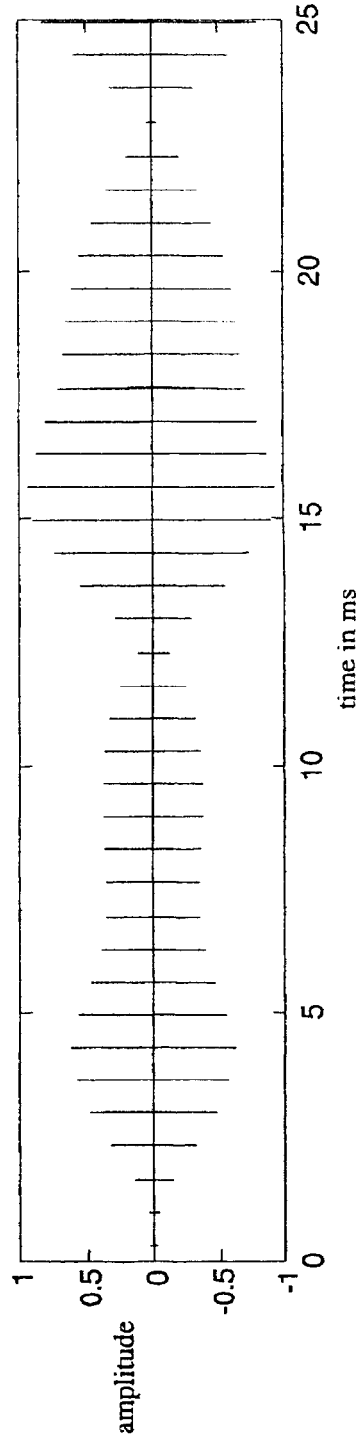

In FIG. 4 stimulation sequences of the new approach are directly compared to the corresponding CIS-sequences at 1.5 kpps. The CSSS-based sequence in FIG. 4(b) clearly represents the temporal fine structure plus the envelope information of the band pass output shown in FIG. 4(a), whereas the CIS-pattern in FIG. 4(c) is obtained by sampling the envelope, and thus any temporal fine structure is removed. At a stimulation channel at higher frequencies, FIGS. 5(b) and (c) are derived by envelope sampling with single pulses. However, in this frequency range, neurons are only able to track the envelope signals, but cannot follow the stimulation frequency itself. The difference between traces 2 and 3 is the sampling rate, which is considerably lower for CIS.

For the practical implementation of the new stimulation approach as described above it is necessary to utilize simultaneous stimulation techniques. Interleaved sampling as employed in CIS is impractical here, since this would require stimulation pulses with a phase duration of only few microseconds.

In the following, the most important mechanisms of channel interaction involved with cochlear implants are summarized.

Channel Interaction

In principle, channel interaction in connection with pulsatile stimulation strategies occurs as a spatial and as a temporal effect. Temporal interaction could be further separated into "physical" and "physiological" interaction.

a. Spatial Channel Interaction

Spatial channel interaction means that there is considerable geometric overlapping of electrical fields at the location of the excitable nervous tissue, if different stimulation electrodes (positioned in the scala tympani) are activated. Thus, neglecting temporal channel interaction, the same neurons can be activated if different electrodes are stimulated. Stimulation of a particular electrode against a remote ground electrode (monopolar stimulation) causes an electrical potential within the scala tympani which can roughly be described by two decaying exponentials at both sides of the electrode, and the space constant (in humans) is typically $\lambda=3.6$ mm, as described by Wilson B. S., Finley C. C., Zerbi M., and Lawson D. T., "Speech processors for auditory prostheses," Seventh Quarterly Progress Report, Feb. 1 through Apr. 30, 1994, NIH Contract N01-DC-2-2401 [hereinafter Wilson et al., 1994], which is incorporated herein by reference. This type of channel interaction is first of all due to the conductive fluids and tissues surrounding the stimulation electrode array. A similar space constant is also obtained by simulation, if a simple model of a cochlea composed of exclusively ohmic resistors is assumed, as described by Kral A., Hartmann R., Mortazavi D., and Klinke R., "Spatial resolution of cochlear implants: the electrical field and excitation of auditory afferents," Hearing Research 121, pp. 11-28, (1998), which is incorporated herein by reference. This model allows a rough quantitative computation of the electrical potentials within the scala tympani, as well as at the position of excitable neurons.

b. Physical Temporal Channel Interaction

Physical temporal channel interaction means that the electrical properties of a stimulation pulse in the nervous tissue are biased by its predecessor, e.g., due to residual charge stored in the tissue and in the membrane capacitances of the neurons. Physical temporal interaction is suppressed to a great extent by using symmetrical, biphasic stimulation pulses. Most of the charge delivered to the excitable tissue during the first phase of a stimulation pulse is removed during the second. However, since the tissue shows some capacitative behavior, some residual charge remains after the end of the stimulation pulse and possibly may bias the subsequent stimulation pulse. Theoretically, triphasic pulses (with zero net charge) would help to further reduce physical temporal channel interaction.

c. Physiological Temporal Channel Interaction

Physiological interaction means effects associated with the refractory properties of the neurons. Following Wilson et al, 1994, a recovery function r(t) can be defined as $$r(t) = 0, \text{ for } t < a, \text{ and } r(t) = 1 - \exp\left(-\frac{t - t_a}{\tau}\right), \text{ for } t > t_a, \quad (1)$$

with an absolute refractory period to $t_a \approx 700$ µs, and a time constant $\tau \approx 1250$ µs for the relative refractory period. For example, if two supra-threshold stimulation pulses are applied, and the second pulse falls into the absolute refractory period after the first, no additional action potential can be elicited. If the second pulse occurs during the relative refractory period, an enhanced amplitude is necessary to generate an action potential.

The influence of physiological temporal interaction on speech understanding is currently investigated at various research centers worldwide. At the moment, it seems that the similarity between neural excitation patterns due to electrical stimulation and natural excitation patterns can be enhanced, if very high stimulation rates are employed (>3 kpps per channel, as described by Matsuoka A. J., "Compound action potentials evoked by electrical pulse trains: effects of stimulus parameters on response patterns," thesis at University of Iowa, (July 1998), which is incorporated herein by reference. High rates may mimic membrane noise (spontaneous activity) and thereby keep different neurons in different refractory states. If this is the case, it can be expected that the ensemble spiking patterns can reflect the envelope of amplitude modulated electrical pulse sequences up to considerably higher frequencies, and thus more temporal information can be provided to the brain.

Consideration of Spatial Channel Interaction

In CIS strategy, the influence of spatial channel interaction is reduced by employing pulses which are not overlapping in time (interleaved sampling). The conductivity in the scala tympani here leads to a considerable spread and a de-focusing of the electrical field at the site of the excitable tissue. However, an additional effect occurs, if simultaneous stimulation of two or more electrodes against a remote ground electrode is considered. Here the conductivity represents a shunt conductance between active electrodes, which in general results in a temporal mixture of constructive and destructive superposition of electrical fields at the position of the neurons. For example, if two simultaneous stimulation channels produce currents with equal amplitudes, but different signs, most of the current will flow through the shunt conductance and will not reach the intended neurons. This additional effect can be removed, if "sign-correlated" pulses are employed. Sign-correlation here means that the signs of the phases of simultaneous stimulation pulses are equal. This ensures that the sum of the magnitudes of the single stimulation currents is forced to flow into the reference electrode. Thus, at the site of the excitable neurons, only constructive superposition of currents is possible.

The injection of a current by means of a single active electrode into the scala tympani causes a particular voltage in the tissue just close to the electrode (measured against the remote reference electrode), and an exponential decay at both sides of the electrode. The space constant typically is $\lambda = 3.6$ mm, as described by Wilson et al, 1994. Assuming a linear and pure ohmic system, the injection of currents in more than one electrode causes a superposition of the potential distributions due to the single currents.

The idea here is to modify stimulation currents such that at least the potentials at the position of the electrodes are equal as in the case of single channel stimulation. Assuming N channels, the single channel (non-simultaneous) current amplitudes $x_n$, (n=1–N) and the amplitudes $y_n$ (n=1–N) for simultaneous channels are related via the following set of linear equations:

$$\begin{pmatrix} x_1 \\ x_2 \\ x_3 \\ \ldots \\ x_{N-2} \\ x_{N-1} \\ x_N \end{pmatrix} = H \begin{pmatrix} y_1 \\ y_2 \\ y_3 \\ \ldots \\ y_{N-2} \\ y_{N-1} \\ y_N \end{pmatrix}, \quad (2)$$

where Matrix H is $$H = \begin{pmatrix} 1 & e^{\frac{-d}{\lambda}} & e^{\frac{-2d}{\lambda}} & \ldots & e^{\frac{-(N-3)d}{\lambda}} & e^{\frac{-(N-2)d}{\lambda}} & e^{\frac{-(N-1)d}{\lambda}} \\ e^{\frac{-d}{\lambda}} & 1 & e^{\frac{-d}{\lambda}} & \ldots & e^{\frac{-(N-4)d}{\lambda}} & e^{\frac{-(N-3)d}{\lambda}} & e^{\frac{-(N-2)d}{\lambda}} \\ e^{\frac{-2d}{\lambda}} & e^{\frac{-d}{\lambda}} & 1 & \ldots & e^{\frac{-(N-5)d}{\lambda}} & e^{\frac{-(N-4)d}{\lambda}} & e^{\frac{-(N-3)d}{\lambda}} \\ \ldots & \ldots & \ldots & \ldots & \ldots & \ldots & \ldots \\ e^{\frac{-(N-3)d}{\lambda}} & e^{\frac{-(N-4)d}{\lambda}} & e^{\frac{-(N-5)d}{\lambda}} & \ldots & 1 & e^{\frac{-d}{\lambda}} & e^{\frac{-2d}{\lambda}} \\ e^{\frac{-(N-2)d}{\lambda}} & e^{\frac{-(N-3)d}{\lambda}} & e^{\frac{-(N-4)d}{\lambda}} & \ldots & e^{\frac{-d}{\lambda}} & 1 & e^{\frac{-d}{\lambda}} \\ e^{\frac{-(N-1)d}{\lambda}} & e^{\frac{-(N-2)d}{\lambda}} & e^{\frac{-(N-3)d}{\lambda}} & \ldots & e^{\frac{-2d}{\lambda}} & e^{\frac{-d}{\lambda}} & 1 \end{pmatrix}, \quad (3)$$

The coefficients of matrix H reflect spatial channel interaction. A coefficient at row i and column j describes the fraction of the single channel potential caused by electrode #j at the position of electrode #i.

For given amplitudes $x_n$, it follows $$\begin{pmatrix} y_1 \\ y_2 \\ y_3 \\ \ldots \\ y_{N-2} \\ y_{N-1} \\ y_N \end{pmatrix} = H^{-1} \begin{pmatrix} x_1 \\ x_2 \\ x_3 \\ \ldots \\ x_{N-2} \\ x_{N-1} \\ x_N \end{pmatrix}, \quad (4)$$

where $H^{-1}$ is the inverse matrix of H. Fortunately, matrix $H^{-1}$ in general is a tri-diagonal matrix with non-zero elements only in the main-, the upper and lower neighboring diagonals (see Section A of the specification).

An example is shown in FIG. 6 for six electrodes (N=6). The x-axis is normalized to a distance d=2.8 mm between the electrodes, i.e., the electrodes are at positions 1 to 6. A space constant λ=3.6 mm is assumed. The y-axis is normalized to the maximum potential of electrode #4 at position 4. FIG. 6(*a*) depicts the single voltage distributions in the scala tympani as responses to single electrode currents at different amplitudes.

For CIS, the electrodes are activated sequentially, and thus each of the single potential distribution applies for the duration of a pulse phase. Assuming a pulse repetition rate of 1.5 kppulses/s for each channel, the overall time necessary to present all six distributions is 666 μs, which is just about the duration of the absolute refractory period ($t_a$≈700 μs). This allows the following rough approximation: for CIS, due to physiological channel interaction, the "effective" stimulation pattern is the contour of the single potential distributions, as shown in FIG. 6(*b*), (asterisks).

If amplitudes $I_{i,CSSS}$ (i=1-6) are computed by means of (4) for a distribution of $I_i$ (i=1-6) as in FIG. 6, one of the current amplitude, $I_{5,CSSS}$, is negative. This is in contradiction to the concept of sign-correlated pulses, which requires the same sign for all simultaneously activated channels. In this case, e.g., the 5th row and 5th column of Matrix H are deleted, resulting in a modified 5×5-Matrix $H_{mod}$. A distribution $I_{i,CSSS,mod}$ with only 5 simultaneous currents is obtained by (1) computing the inverse matrix $H^{-1}_{mod}$, and (2) multiplying $H^{-1}_{mod}$ with vector $I_i$ (i=1, 2, 3, 4, and 6). The resulting potential distribution is shown in FIG. 6(*b*), (circles). As demanded, the potentials coincide at the positions 1, 2, 3, 4, and 6. Obviously, the peaks obtained by taking the contour of the non-simultaneous potential distributions CIS are more pronounced than with CSSS.

Figure 7A:
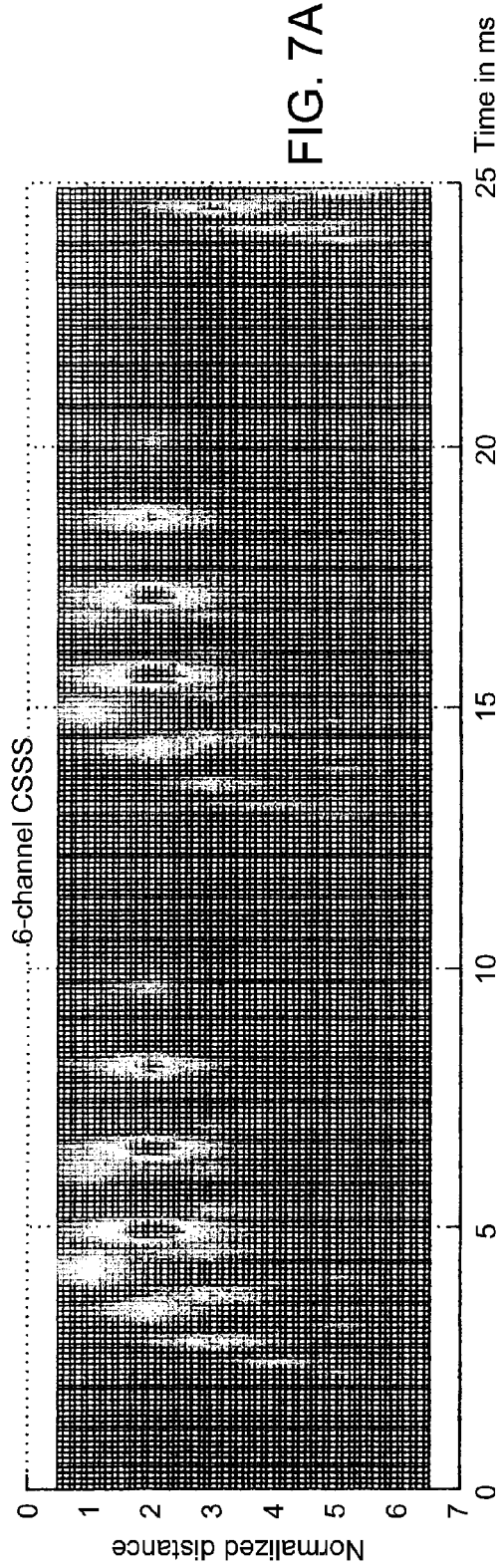
FIG. 7 shows a comparison of overall stimulation patterns between CSSS and CIS (electrode distance: d=2.8 mm, space constant: $\lambda$=3.6 mm)
   a. 6-channel CSSS
   b. 6-channel CIS
Figure 7B:
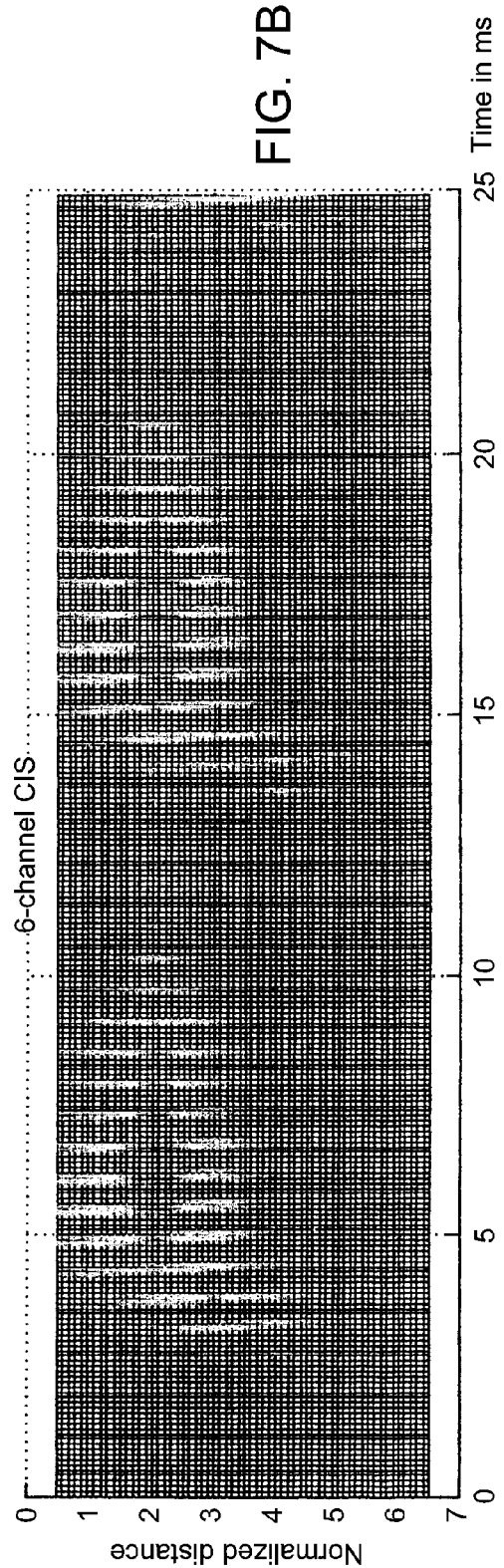

For the CSSS system, FIG. 7(*a*), the envelope sampling sequences for each channel are chosen as shown in FIG. 1(*a*). To obtain the actual stimulation signals for each channel, the spatial channel interaction is taken into account. As expected, the stimulation pattern reflects the temporal fine structure. In particular, the center frequency of channel #2 is represented in the temporal waveform. A so-called "hole-effect" can be observed: if electrode #2 is not active, i.e., if the output of filter channel #2 is negative, then other spectral maxima are not masked (due to spatial channel interaction) and appear in the waveform.

The CIS system, FIG. 7(*b*) is based on an overall sampling rate of 10 kpps, resulting in a rate of 1667 pps per channel for the 6-channel system. Envelope detection for each channel is achieved with a full-wave rectifier and a low pass filter with a cut off frequency of 400 Hz (Butterworth filter of 2nd order), respectively. Obviously, the envelope signal is sampled and presented, but the temporal fine structure is lost.

Implementation of a Cochlear Implant System Based on CSSS

Although based on highly synchronous stimulation, the CSSS approach is well suited for an implementation in a practical cochlear implant system. The information transfer rate from the speech processor to the implant can be kept comparatively low. An example of a data word for a 12-channel CSSS system is shown in Tab.1.

One data word consists of 16 bits, including START and STOP bits. The two special bits SPEC1 and SPEC0 represent a low rate information channel and are used for the initialization of the implant. The implant is permanently supplied with data defining the amplitude distributions and pules repetition rate of the normalized CSSS's, as well as data defining the reference current levels for each channel. These data are stored in particular implant memories. Besides, safety bits (e.g., for cyclic redundancy check (CRC)) are transmitted. Note that for proper operation of the implant, the information defining the normalized CSSS's and the reference current levels theoretically have to be transmitted only once.

The four address bits ADD3-ADD0 define the channel address, and bits W7-W0 the weighting factor of the associated CSSS. The repetition rate of the

TABLE 1

Data word

| Bit # | Definition |
|---|---|
| 1 | START |
| 2 | ADD3 |
| 3 | ADD2 |
| 4 | ADD1 |
| 5 | ADD0 |
| 6 | W7 |
| 7 | W6 |
| 8 | W5 |
| 9 | W4 |
| 10 | W3 |
| 11 | W2 |
| 12 | W1 |
| 13 | W0 |
| 14 | SPEC1 |
| 15 | SPEC0 |
| 16 | STOP |

CSSS's is comparatively low, especially at the low frequency channels. It is not necessary to transmit the amplitudes of the individual ultra-high rate pulses, since the amplitude distributions are already stored in the implant.

Assuming an input analysis range between 350 Hz-5500 Hz for a 12-channel system, and a logarithmic spacing of the band pass filter ranges, results in center frequencies 393 Hz, 494 Hz, 622 Hz, 782 Hz, 983 Hz, 1237 Hz, 1556 Hz, 1958 Hz, 2463 Hz, 3098 Hz, 3898 Hz, and 49036 Hz. Thus, the average CSSS-repetition rate is equal to the sum of the center frequencies, i.e., $R_{CSSS}$=22386 Hz. This is equal to the average data word repetition rate $R_{dataword}$. The resulting average overall bit rate is $R_{bit}$=16$R_{dataword}$≈358 kbit/s. Thus, a bit rate of 600 kbit/s for a practical cochlear implant is sufficient for complete information transfer. However, this is a moderate rate as compared to the case, if each stimulation pulse has to be defined independently. Here, assuming a frame-rate of 10 kpps of simultaneous stimulation pulses and a data word of 16 bit per pulse, an overall bit rate of 1920 kbit/s results. Such a bit rate is almost impossible to realize with a inductive link system at reasonable power consumption.

Within the implant, the correction of the amplitudes due to spatial channel interaction has to be performed for each simultaneous stimulation frame.

SUMMARY

In summary, the CSSS stimulation approach may be summarized as follows.

(1) For stimulation, a multichannel electrode array within the scala tympani and a remote ground electrode is used (monopolar electrode configuration). The basic stimulation waveform is a symmetrical, biphasic pulse.

(2) Stimulation involves simultaneous activation of electrodes in the scala tympani employing sign-correlated pulses. Sign-correlated means that if two or more pulses occur simultaneously at different electrodes, positive and negative phases are absolute synchronous in time.

(3) The amplitudes of the sign-correlated pulses are estimated by taking into account parameters of spatial channel interaction. Assuming that a single electrode causes exponential decays of the potentials at both sides of the electrode allows a computationally efficient calculation of the pulse amplitudes, since a tri-diagonal matrix is involved.

(4) Processing of the acoustic signal involves a filter bank for splitting up the audio frequency range (similar to CIS). According to the tonotopic organization of the scala tympani, each band pass filter is associated with a stimulation electrode.

(5) Each stimulation channel is associated with a normalized, channel specific sampling sequence (CSSS) of ultra-high-rate pulses. Typically, rates between 5-10 kpps are employed. For each channel, the CSSS has different length and different amplitude distribution. The maximum amplitude of a normalized CSSS is one.

(6) The length of a CSSS is derived from the center frequency of the associated band pass filter. Typically, it is one half of the period of the center frequency. For example, a band pass center frequency of 500 Hz results in a CSSS-length of 1 ms comprising 10 pulses. (assuming a ultra-high-rate of 10 kpps).

(7) The amplitude distribution of a CSSS is chosen for optimum performance with respect to mimicking membrane noise. As many neurons as possible shall be kept in different refractory states.

Although various exemplary embodiment of the invention have been disclosed, it should be apparent to those skilled in the art that various changes and modifications can be made which will achieve some of the advantages of the invention without departing from the true scope of the invention. These and other obvious modifications are intended to be covered by the claims that follow.

Section A

The matrix product (2) can be regarded as a convolution product of an infinite sequence $h_n$ and a sequence $y_n$, with non-zero elements only at positions n=1, 2, ... N, i.e., $$x_n = h_n * y_n, \quad (A1)$$

where sequence $h_n$ is given by $$h_n = \alpha_n u_n + \alpha^{-n} u_{-n-1}. \quad (A2)$$

Function $u_n$ is the unit step, i.e., $u_n=1$ for $n \geq 0$, and $u_n=0$ for n<0. Sequence $h_n$ represents an infinite impulse response (IIR) with exponential decays at both sides of the origin ($|\alpha|<1$). The z-transform is given by $$H(z) = \frac{1}{(1-\alpha z^{-1})} + \frac{-1}{(1-\alpha^{-1}z^{-1})}, \quad (A3)$$

which can be expressed as $$H(z) = \frac{\left(\alpha + \frac{1}{\alpha}\right)}{\left(z^{+1} - \left(\alpha + \frac{1}{\alpha}\right) + z^{-1}\right)}. \quad (A4)$$

Transformation of (A1) into the z-domain yields $$X(z) = H(z)Y(z), \quad (A5)$$

and thus $$Y(z) = H^{-1}(z)X(z). \quad (A6)$$

Inserting (A4) yields $$Y(z) = \frac{1}{\left(\alpha + \frac{1}{\alpha}\right)}\left(z^{+1} - \left(\alpha + \frac{1}{\alpha}\right) + z^{-1}\right)X(z). \quad (A7)$$

The inverse z-transform immediately yields $$y_n = \frac{1}{\left(\alpha + \frac{1}{\alpha}\right)}\left(\delta_{n+1} - \left(\alpha + \frac{1}{\alpha}\right)\delta_n + \delta_{n-1}\right) * x_n, \quad (A8)$$

where $\delta_n$ is the unit impulse, i.e., $\delta_n=1$ for n=0, and $\delta_n=0$ elsewhere. The first term of the convolution product (A8) is a finite impulse response (FIR). Equation (A8) can be expressed as $$y_n = \frac{1}{\left(\alpha + \frac{1}{\alpha}\right)}\left(x_{n+1} - \left(\alpha + \frac{1}{\alpha}\right)x_n + x_{n-1}\right), \quad (A9)$$

which is a set of linear equations. To calculate $y_n$ at positions n=1 and n=N requires to know amplitudes $x_0$ and $x_{N+1}$. Since sequence $y_n$ can have non-zero elements only at positions n=1, 2, ... N, it follows with (A1)

$$x_0 = y_1\alpha y_2\alpha^2 + \ldots + y_N\alpha^N = \alpha(y_1 + y_2\alpha^1 + \ldots + y_N\alpha^{N-1}) = \alpha x_1, \quad (A10)$$

and similarly $$x_{N+1} = y_1\alpha^N + y_2\alpha^{N-1} + \ldots + y_N\alpha = \alpha(y_1\alpha^{N-1} + y_2\alpha^{N-2} + \ldots + y_N) = \alpha x_N, \quad (A11)$$

Inserting $x_0$ and $x_{N+1}$ in (A9) for n=1 and n=N allows to write (A9) as matrix equation, and the matrix necessarily has to be identical to the inverse matrix of H:

$$\begin{pmatrix} y_1 \\ y_2 \\ y_3 \\ \vdots \\ y_{N-2} \\ y_{N-1} \\ y_N \end{pmatrix} = H^{-1} \begin{pmatrix} x_1 \\ x_2 \\ x_3 \\ \vdots \\ x_{N-2} \\ x_{N-1} \\ x_N \end{pmatrix}, \quad (A12)$$

where matrix $H^{-1}$ is a tri-diagonal matrix given by $$H^{-1} = \begin{pmatrix} b_0 & -a & 0 & \cdots & 0 & 0 & 0 \\ -a & b & -a & \cdots & 0 & 0 & 0 \\ 0 & -a & b & \cdots & 0 & 0 & 0 \\ \cdots & \cdots & \cdots & \cdots & \cdots & \cdots & \cdots \\ 0 & 0 & 0 & \cdots & b & -a & 0 \\ 0 & 0 & 0 & \cdots & -a & b & -a \\ 0 & 0 & 0 & \cdots & 0 & -a & b_0 \end{pmatrix}, \quad (A13)$$

with coefficients $$b_0 = \frac{1}{\left(\frac{1}{\alpha} - \alpha\right)} \frac{1}{\alpha}, \quad (A14)$$

$$b = \frac{1}{\left(\frac{1}{\alpha} - \alpha\right)} \left(\alpha + \frac{1}{\alpha}\right),$$

-continued and $$a = \frac{1}{\left(\frac{1}{\alpha} - \alpha\right)}.$$

It shall be mentioned that the analysis can simply be expanded to the case, if the infinite sequence $h_n$ (A2) is of the form $$h_n = \alpha^n u_n + \beta^{-n} u_{-n-1}, \quad (A15)$$

i.e., the exponential decays are different for n>0 and n<0 ($|\alpha|<1$, $|\beta|<1$).

In the following, it is assumed that for a given vector $x_n$ with $x_n>0$ for all n (n=1, 2, ... N), equation (3) yields a vector $y_n$ containing negative elements at positions k, i.e., $y_k<0$. Negative elements mean negative current amplitudes, which are in contradiction to the principle of sign-correlation, and therefore have to be avoided.

One method of handling such a case is to compute a new vector $y'_n$, where the elements at the positions k are set to zero, i.e., $y'_{n+k}=0$. This restriction requires a modified input vector $x'_n$. In the proposed method, $x'_n$ differs from vector $x_n$ only at positions k and remains unchanged elsewhere, i.e., $x'_{n \neq k}=x_{n \neq k}$, and $x'_{n=k} \neq x_{n=k}$.

It is claimed that conditions $$y'_{n=k}=0, \text{ and } x'_{n \neq k}=x_{n \neq k} \quad (A16)$$

yield a definite solution for vector $x'_n$ at all positions.

To prove this claim for an arbitrary pattern of k, "zero-sequences" of neighboring indices within k of length L are regarded. For convenience, the smallest index within each zero-sequence is designated as starting index k0. For example, for N=12, and assuming a pattern k=[1, 2, 5, 6, 7, 10], three zero-sequences [1, 2], [5, 6, 7], and [10] with lengths L=2, 3, and 1 can be identified, and the starting indices are 1, 5, and 10, respectively. A zero-sequence of length L=1 is also designated as "sequence".

Two categories have to be distinguished:
Category (1): a zero-sequence does not contain indices 1 or N, and
Category (2): a zero-sequence contains either index 1 or N.

For the example of above, zero-sequence [1, 2] belongs to category (2), zero-sequences [5, 6, 7], and [10] belong to category (1).

ad Category (1): here, for a given zero-sequence, neighboring elements with positive $y_n$ at the lower- and the upper range of a zero-sequence do exist at positions n=k0−1 and n=k0+L, respectively. For example, for N=12 and a zero-sequence [5, 6, 7], k0=5, and L=3, and thus the neighboring positions are n=4 and n=8.

Setting $y'_{n=k}=0$ yields the following set of equations:

$$0 = -ax_{k0-1} + bx'_{k0} - ax'_{k0+1} \quad (A17)$$
$$0 = \quad\quad\quad -ax'_{k0} + bx'_{k0+1} - ax'_{k0+2}$$
$$\cdots \quad\quad\quad \cdots$$
$$0 = \quad\quad\quad -ax'_{k0+L-3} + bx'_{k0+L-2} - ax'_{k0+L-1}$$
$$0 = \quad\quad\quad\quad\quad -ax'_{k0+L-2} + bx'_{k0+L-1} - ax_{k0+L}.$$

Elements $x_{k0-1}$ and $x_{k0+L}$, and coefficients a and b are known, and thus for L>1, (A17) can be written as $$\begin{pmatrix} x'_{k0} \\ x'_{k0+1} \\ x'_{k0+2} \\ \cdots \\ x'_{k0+L-3} \\ x'_{k0+L-2} \\ x'_{k0+L-1} \end{pmatrix} = \frac{1}{a} Q_L^{-1} \begin{pmatrix} x_{k0-1} \\ 0 \\ 0 \\ \cdots \\ 0 \\ 0 \\ x_{k0+L} \end{pmatrix} \quad (A18)$$

with matrix square $Q_L$ $$Q_L = \frac{1}{a^2} \begin{pmatrix} b & -a & 0 & \cdots & 0 & 0 & 0 \\ -a & b & -a & \cdots & 0 & 0 & 0 \\ 0 & -a & b & \cdots & 0 & 0 & 0 \\ \cdots & \cdots & \cdots & \cdots & \cdots & \cdots & \cdots \\ 0 & 0 & 0 & \cdots & b & -a & 0 \\ 0 & 0 & 0 & \cdots & -a & b & -a \\ 0 & 0 & 0 & \cdots & 0 & -a & b \end{pmatrix}. \quad (A19)$$

The number of lines (and rows) of matrix $Q_L$ is L (L>1). Note that amplitudes $x'_k$ are fully determined by the "neighboring" amplitudes $x_{k0-1}$ and $x_{k0+L}$. In particular, amplitudes $x'_{k0}$ and $x'_{k0+L-1}$ can be calculated with $$x'_{k0} = \frac{c^{(L)}}{a} x_{k0-1} + \frac{d^{(L)}}{a} x_{k0+L}, \quad (A20)$$

and $$x'_{k0+L-1} = \frac{d^{(L)}}{a} x_{k0-1} + \frac{c^{(L)}}{a} x_{k0+L},$$

where coefficients $c^{(L)}$ and $d^{(L)}$ are the elements at the left- and right upper corner of matrix $Q^{-1}$, respectively, i.e., at matrix positions (1,1) and (1,L). For each length L, there exists one unique pair of coefficients $c^{(L)}$ and $d^{(L)}$. For L=1, evaluation of (A17) yields $$c^{(1)} = c^{(2)} = \frac{a^2}{b}.$$

With (A20), the amplitudes $y'_{k0-1}$ and $y'_{k0+L}$ can be determined:

$$\begin{aligned} y'_{k0-1} &= -ax_{k0-2} + bx_{k0-1} - ax'_{k0} = \\ &= -ax_{k0-2} + (b - c^{(L)})x_{k0-1} - d^{(L)}x_{k0+L}, \end{aligned} \quad (A21)$$

and $$\begin{aligned} y'_{k0+L} &= -ax'_{k0+L-1} + bx_{k0+L} - ax_{k0+L+1} = \\ &= -d^{(L)}x_{k0-1} + (b - c^{(L)})x_{k0+L} - ax_{k0+L+1}. \end{aligned}$$

Thus, setting the amplitudes $y'_k=0$ for a zero-sequence results in a modification of the elements in $y_n$ only at positions, which are neighboring to the zero-sequence. Note that other elements of $y_n$ are not concerned. Equation (A21) can be implemented by means of the following steps:

(1) replace coefficients $-a$, $b$, and $-a$ in line k0-1 by $-a$, $b+c^{(L)}$, and $-d^{(L)}$,
(2) replace coefficients $-a$, $b$, and $-a$ in line k0+L by $-d^{(L)}$, $b+c^{(L)}$, and $-a$,
(3) delete lines and rows with indices k from matrix $H^{-1}$, and remove elements with indices k from vector $x_n$.

ad case (2): if a zero-sequence contains index 1, the modified amplitudes are exponentials up to index L (cf. (A10)), and can be derived from amplitude $x_{L+1}$:

$$\begin{pmatrix} x'_1 \\ x'_2 \\ \cdots \\ x'_L \end{pmatrix} = \begin{pmatrix} \alpha^L x_{L+1} \\ \alpha^{L-1} x_{L+1} \\ \cdots \\ \alpha x_{L+1} \end{pmatrix}. \quad (A22)$$

Regarding the matrix operation, the coefficient b of line L+1 of $H^{-1}$ has to be replaced by coefficient $b_0$. Then all lines and rows with indices k have to be removed, and the elements of $x_n$, with indices k can be ignored.

Similarly, if a zero-sequence contains index N, the modified amplitudes are exponentials for indices greater than k0+L and can be derived from amplitude $x_{k0-1}$:

$$\begin{pmatrix} x'_{k0} \\ x'_{k0+1} \\ \cdots \\ x'_N \end{pmatrix} = \begin{pmatrix} \alpha x_{k0-1} \\ \alpha^2 x_{k0-1} \\ \cdots \\ \alpha^L x_{k0-1} \end{pmatrix}. \quad (A23)$$

Regarding the matrix operation, the coefficient b of line k0−1 of $H^{-1}$ has to be replaced by coefficient $b_0$. Then all lines and rows with indices k have to be removed, and the elements of $x_n$ with indices k can be ignored.

Theoretically, vector $y'_n$ can again contain negative elements, but the magnitude of the negative elements are comparatively small. A repetition of the proposed procedure could remove them, but in many cases, it is sufficient to replace the negative elements by zeros and neglect the impact.

Based on the analysis of above, the following computational efficient procedure for the consideration of channel interaction in an N channel system can be applied.

(1) Compute $y_n$ by multiplication of $H^{-1}$ and $x_n$.
(2) Select elements $y_{n=k}<0$ and set $y_k'=0$.
(3) Modify elements of $H^{-1}$ according to (A21), (A22), (A23)
(4) Remove all lines and rows of $H^{-1}$ with indices k, and remove all elements $x_k$.
(5) Compute elements $y_n'$, which are neighboring to zero-sequences.

EXAMPLE

Let the result of the matrix multiplication $y_n = H^{-1} x_n$ (matrix $H^{-1}$ defined by coefficients $b_0$, b, and a, for a 12-channel system (N=12) be a vector containing negative elements at positions k=[1, 2, 6, 7, 9, 10, 11]. Then the modified vector $y'_n$ is $$y'_n = \begin{pmatrix} 0 \\ 0 \\ y'_3 \\ y'_4 \\ y'_5 \\ 0 \\ 0 \\ y'_8 \\ 0 \\ 0 \\ 0 \\ y'_{12} \end{pmatrix}, \quad (A24)$$

and the unknown elements are computed by $$\begin{pmatrix} y'_3 \\ y'_4 \\ y'_5 \\ y'_8 \\ y'_{12} \end{pmatrix} = \begin{pmatrix} b_0 & -a & 0 & 0 & 0 \\ -a & b & -a & 0 & 0 \\ 0 & -a & b-c^{(2)} & -d^{(2)} & 0 \\ 0 & 0 & -d^{(2)} & b-c^{(2)}-c^{(3)} & -d^{(3)} \\ 0 & 0 & 0 & -a & b \\ 0 & 0 & 0 & -d^{(3)} & b_0-c^{(3)} \end{pmatrix} \begin{pmatrix} x_3 \\ x_4 \\ x_5 \\ x_8 \\ x_{12} \end{pmatrix}. \quad (A25)$$

Note that element $y'_4 = y_4$, because position $n=4$ is not neighboring to a zero-sequence. Element $y'_8$ is neighboring to two zero-sequences. Therefore, the corresponding element in the main diagonal is $b-c^{(2)}-c^{(3)}$, reflecting the influence of both zero-sequences. Coefficients $c^{(2)}$, $d^{(2)}$ and $c^{(3)}$, $d^{(3)}$ are computed by inverting matrices $Q_2$ and $Q_3$, which themselves only depend on coefficients a and b.

What is claimed is:

1. A system for activating electrodes, the system including:
   a multi-channel electrode array;
   a stimulator for activating electrodes in the electrode array using channel specific sampling sequences;
   a signal processor including a filter bank for receiving an acoustic representative electrical signal, each filter in the bank of filters associated with one of the electrodes in the multi-channel electrode array, each electrode in the multi-channel electrode array associated with a different channel specific sampling sequence,
   wherein the channel specific sampling sequence has a predefined duration, amplitude, plurality of pulses and pulse rate, the duration and number of pulses in each channel specific sampling sequence derived from the center frequency of the associated band pass filter, and
   wherein a weighting factor is applied to each channel specific sampling sequence so as to create a weighted channel specific sampling sequence for each electrode in the electrode array, the weighting factor based, at least in part, on an acoustic representative electrical signal.

2. The system according to claim 1, wherein the channel specific sampling sequence pulse amplitude is derived by sampling a signal waveform, the signal waveform different from the acoustic representative electrical signal.

3. The system according to claim 2, wherein the signal waveform is one of a half period of a sinusoid between 0 and π, and a quarter period of a sinusoid between 0 and π/2.

4. The system according to claim 1, wherein the channel specific sampling sequence has a pulse rate between 5-10 kpps.

5. The system according to claim 1, wherein the stimulator simultaneously activates each electrode using sign-correlated pulses.

6. The system according to claim 5, wherein the amplitudes of the sign-correlated pulses are based, at least in part, on parameters of spatial channel interaction, wherein calculating the amplitudes of the sign-correlated pulses includes compensating for geometric overlapping of electric fields from each electrode.

7. The system according to claim 1, wherein the signal processor determines the weighting factor for each channel specific sampling sequence.

8. The system according to claim 7, wherein the signal processor derives the weighting factor for each electrode in the multi-channel electrode array from an associated channel filter.

9. The system according to claim 8, further comprising a rectifier for rectifying the output of each filter to create a half-wave rectified signal, wherein the signal processor determines a maximum amplitude of each half-wave in the half-wave rectified signal.

10. The system according to claim 9, wherein each half-wave is replaced by the channel specific sampling sequence associated with the electrode, with the amplitude of the maximum pulse within the channel specific sampling sequence associated with the electrode equal to the maximum amplitude.

11. The system according to claim 1, further comprising a radio frequency link between the signal processor and the stimulator.

12. The system according to claim 1, wherein each filter is a bandpass filter.

13. The system according to claim 1, wherein the duration of the channel specific sampling sequence is one half of the period of the bandpass filter's center frequency.

14. The system according to claim 1, wherein the system includes a cochlear implant capable of stimulating the acoustic nerve.

15. A method of defining a channel specific sampling sequence having a pulse descriptive characterization, the channel specific sampling sequence being used to activate electrodes in a multichannel electrode array, each filter in a bank of filters associated with a channel having an electrode, the method comprising:
    deriving pulse amplitudes of the channel sampling sequence by sampling a signal waveform;
    deriving the duration and number of pulses of the channel specific sampling sequence from a frequency associated with the channel's filter.

16. A method according to claim 15, wherein the sampling is one of a half period of a sinusoid between 0 and π, and a quarter period of a sinusoid between 0 and π/2.

17. A method according to claim 15, wherein the sampling uses biphasic current pulses.

18. A method according to claim 15, wherein each filter is a bandpass filter.

19. A method according to claim 18, wherein the duration and number of pulses in the channel specific sampling sequence is derived from the center frequency of the channel's bandpass filter.

20. A method according to claim 19, wherein the duration of the channel specific sampling sequence is one half of the period of the bandpass filter's center frequency.

* * * * *